United States Patent [19]

Hechler, IV

[11] 4,020,977
[45] May 3, 1977

[54] CONTINUOUS FLOW RATIO MONITOR

[76] Inventor: Valentine Hechler, IV, 26 Meadow View Road, Northfield, Ill. 60093

[22] Filed: Jan. 26, 1976

[21] Appl. No.: 652,378

Related U.S. Application Data

[62] Division of Ser. No. 482,353, June 24, 1974, Pat. No. 3,938,550.

[52] U.S. Cl. .............................. 222/145; 222/159
[51] Int. Cl.² .......................................... G01N 1/20
[58] Field of Search ............. 222/145, 57, 95, 159; 239/74, 320; 137/559, 604

[56] References Cited

UNITED STATES PATENTS

3,938,550  2/1976  Hechler .............................. 239/74

Primary Examiner—Stanley H. Tollberg
Attorney, Agent, or Firm—Watson D. Harbaugh

[57] ABSTRACT

A solution dispensing proportioner utilizing a varyingly pressurized solvent and a solute having a vagrant negative gauge pressure and a tracer that is detectable in proportion to its concentration. The proportioner aspirates the solute and tracer through a conduit, which may have metering flow valves ahead of the confluence in one embodiment, and then for a progressive check of the proportion of the solution after confluence by comparing the light transmissivity of the inflowing solute and the outflowing solution, respectively. The viewing is through windows in close proximity to each other where the relative depths of the flowing streams of solute and solution, as viewed, are substantially inversely proportional to the desired percentage of solute in the solution as corrected for a null point traverse by adjusting the solute valve to provide the ratio desired for the solute and solvent in the final solution. The tracer supply is variable to optimize the null point appraisal.

5 Claims, 25 Drawing Figures

CONTINUOUS FLOW RATIO MONITOR

This is a division, of application Ser. No. 482,353, filed on June 24, 1974, now U.S. Pat. No. 3,938,550.

CROSS REFERENCES

Hechler, U.S. Pat. No. 3,431,941, issued Mar. 11, 1969
Hechler Ser. No. 443,831, filed Feb. 19, 1974
Hechler, Ser. No. 418,899, filed Nov. 26, 1973
Hechler, Ser. No. 333,309, filed Feb. 16, 1973

BACKGROUND OF INVENTION

Heretofore, the proportioning and dispensing of liquids has had to depend essentially upon batch mixtures of pre-measured ingredients, with their accompanying usual unused overage waste, if any degree of accuracy is required, or, upon aspirating hand sprayers where accuracy is immaterial. Moreover, aspiration and entrainment of a solute must be accomplished after discharge directly to the air to avoid backflow contamination condemned in most states.

The pressure upon the solute in conventional nonpositive displacement type dispensers is vagrant. It can range rather widely down to a deep vacuum depending on the lift height from the solute supply or its controlled flow rate. Also, undesirable degradation of the ratio can occur in continuous flow mixes with any variation in the pressure of either the solvent or solute, or both, which sometimes occur with depletion. Although momentary or slight changes may not be serious because ratio accuracy can be objectionably degraded unless carefully watched when using a municipal water supply system that might have a wide range of pressures and with different solute supplied stored in containers.

Rapid, accurate and reliable ratio and monitoring adjustments are desired but have not been available, particularly with the serious degradation of the ratio occurring with recurrent clogging of the solute supply or with proportioners of the aspirating type.

Moreover, when utilizing municipal water pressure, many continuous proportioning, instant mixing and dispensing devices can tolerate but very little pressure change without a correcting means because many municipal pressures are already quite low. Even a slight change can make a big difference in accuracy with wide variation in water pressure.

In correct those difficulties, the user must be able to monitor and control the ratio intermittently or continuously and accurately; the apparatus must be portable and readily viewed; should be easily readable and preferably utilize ambient light for illumination. Moreover, it should provide a continuously fresh sampling and quick read-out, if desired, to indicate any ratio degradations occurring and permit rapid null point traverse corrections.

Structurally and functionally, the instrument must be substantially attitude and altitude insensitive; capable of a self-purging of any foreign matter in all sections of its assembly, namely, the solvent and solute supply sections and the solution output sections; and, desirably, must be light, rugged, and easily handled.

Moreover, as disclosed in said Hechler applications, with the development of aspirating sprayers which are acceptable for utilizing various municipal water pressures because they do not create backflow contamination problems, a wide range of solutions at various ratios can now be applied, many of which due to potency or criticality require quite accurate ratio indication and control if control is possible.

SUMMARY OF THE INVENTION

In the present invention a device is disclosed for mixing a solute stream and a solvent stream both of which may be at fluctuating pressures and flow rates, to produce a flowing solution of desired concentration and means are provided for optically monitoring energy transmitting properties of the effluent solution with those of the incoming solute stream itself regardless of variations in its tracer intensity of concentration. Both of the streams pass separately through individual transparent chambers. The depth of the solute chamber, which is adjustable, constitutes that fraction of the depth of the solution chamber whereby the light transmitting properties of both are substantially the same at the desired mixing ratio for the ingredients, the flow rate of at least one of the liquids being adjustable to assure this in the solution.

With the present invention the tracer concentrate can be shipped and used either directly or with a dilution thereof, in any determined ratio, to form the solute to be used or, since many solutes are not furnished with tracers, and even though some are, the present invention further contemplates supplying a tracer to the solute and, if desired, varying the amount of tracer to optimize its visual comparison level either for a continuous monitoring of the desired proportion ratio or for a periodic check, the actual quantity of tracer used at any given time being otherwise inconsequential. Thereafter, knowing the desired sprayer dispensing ratio, either one of two embodiments can be employed. For instance, where the ratio is to be constant, either a spacer rated for that ratio can be positioned between the solute viewing window and a background light-diffusing window of the solute chamber to provide an exactly known chamber depth or space through which the solute flows before confluence, or, the known depth of the chamber can be manually varied at will for monitoring a range of different ratios. Moreover, a prism arrangement can be used to brind perception of the comparison windows close together for one eye for sharper null point comparison of the solution and solute used therewith without moving the monitor back and forth with respect to the eye.

In these embodiments, a flow rate control valve may be located between the solute viewing chamber and a source of a rapidly flowing colored solute supply. Then comparably if the tracer appears darker in the solute chamber than that in the solution viewing chamber, the solution is "lean" and the valve is adjusted in an opening direction until the tracer effects match in transmissivity. On the other hand, if the color in the solution chamber is darker, the solution is too "rich" and the valve is adjusted in the closing direction until the tracer effects match in appearance. Thereby the effect of the valve is continuous and quickly ascertained.

On the other hand, when the embodiments are used as a monitor for low flow rates the relative depths can be varied to determine the existing ratio of a particular solution as related to a depth scale. Then, if there is a slight mismatch manual exploration can indicate what the unknown ratio is. When the tracer effects match, the ratio is correct or determined; namely, that which is indicated by the relative depths, or, the valve adjustment, has been accomplished for a particular adjustment.

It will be appreciated that treated windows can be used which with the energy transmissivity of the tracer provides a shade of darkness and color blend observation.

In order to provide a wide range of adjustments the depth of the solution chamber us preferably determined to be as great as possible to handle a low ratio as well as a quite high ratio of mixtures. For instance, the one inch depth in the solution chamber will enable a 0.010 spacing in the solute chamber to check a 1 to 99 ratio in the manner above indicated. Two and 3 inch depths may be readily provided and the adjustment range of solute chamber thereby extended. If solutes or solutions dispensed are to be a fixed ratio, spacer disks can be used. Possible variations or fading of tracers from batch to batch is non-consequential. The matching of the tracer is against itself as its own continuing standard.

More particularly, an object of this invention by way of example is to provide an optical monitor that operates continuously and provides a substantially immediate indication as to the correctness of the ratio regarding the number of parts of solute to the number of parts of solvent in the solution being mixed. This is accomplished by means of a relative comparison of the tracer effects of a solute pre-treated with a tracer with those of a solution of said solute as both pass through windowed scanning chambers for light i.e. detectable energy transmissivity comparison where the relative depths of the liquids in the chambers are in the desired ratio. The checking is irrespective of the tracer used, its intensity or a variation as long as it can absorb as well as transmit detectable energy such as light through the solute chamber.

Other objects include a visual monitor which is simple in construction, light enough to be mounted on a hand held dispenser, and can be easily cleaned, purged and serviced by owners unskilled mechanically, for use with a wide range of chemicals in which the user has the discretionary control over the performance and operation as well as accuracy of the device and solution.

A further object of the invention is to provide a tracer injecting device for solutes lacking a tracer for the purposes of proportioning and comparing, no degree of its dispensing accuracy being necessarily required other than to optimize the comparison at the monitoring windows which can vary substantially without actually affecting the accuracy of the comparison and the ratio.

DESCRIPTION OF INVENTION

SOLVENT SUPPLY AND FLOW CONTROL

Figure 1:
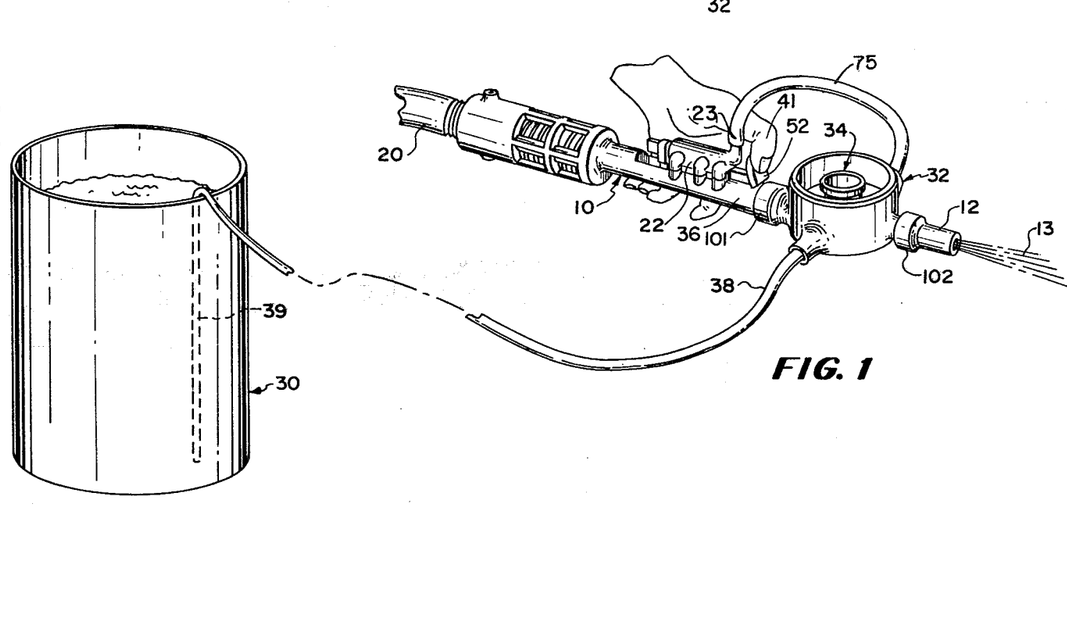
FIG. 1 is a perspective view of a device with a comparator embodiment of the invention in operative position as manipulated in use..

As more particularly disclosed in the foregoing Application for Letters Patent and referring to FIG. 1 herein, a portable mixing and dispensing device 10, used for soft flow output without a nozzle or for a hard stream discharge with a nozzle 12, has a unitary housing 11 providing an anti-contamination venting chamber 16, mounted in the chamber automatically interacting flow control vent valves 14A and 14B, and a manual control valve 18 along with a backflow check valve 15 having a common seat member 15A between them to selectively control forward flow and automatically prevent backflow therethrough. They operate to provide flow only when the solvent (water) supply pressure is above a predetermined positive working gauge pressure and vent the chamber when the pressure falls below a predetermined gauge pressure while there still is substantial gauge pressure present in the chamber, thus providing a positive flow during operation yet preventing any possibility of backflow until the chamber is fully vented to prevent it.

Also a solute supply valve 22 connected to a solute supply is provided that is selectively actuatable simultaneously with the manual flow control valve 15 so that either plain solvent or a wide variety of chemical solutions can be discharged merely by selective engagement at 17 of the solute flow control valve 79 as later described with the solvent control valve 18.

In controlling the solvent flow the outer end of the main valve stem 18A extends in an axial direction through an opening 42 in a cross-wall portion 43 having a V-ring seal therein which seals the stem as terminally exposed to atmosphere in the housing recess 46. As disclosed and described in Hechler Ser. No. 418,899, manual actuation of the flow control valve assembly is by push rod 48 reciprocably mounted on the housing 11. The front end of the push rod 48 is reversely formed to provide a thumb handle 52 and the rear end carries a T-shaped head 50 thereon whose lower end engages the valve stem and actuates the valve stem portion 18A where it projects into the recess 46.

A full flow passage from the solvent flow control and check valves leads around the recess 46 and leads to a downstream chamber 21 in which the jet pump 24 having two sections 24A and 24B that operate in tandom within a unitizing shell 54 handles different chemicals and proportions. The jet pump 24 is terminally sealed and held in the housing between seals 55, by either the nozzle 12, or the monitor 156, and a collar 58 received on the respective end thread 60 of the housing 11 or monitor 32. The space around the jet pump assembly 24 serves as a solute receiving chamber.

Furthermore, for purposes of illustration, representative embodiments of a series arrangement is shown herein connected to the outlet of a garden hose 20 to utilize municipal water as a source of solvent whose pressure ranges from 15 to 100 p.s.i.g. Variations in this pressure can further vary the ratios of the resulting solutions. These variations compound the difficulty of maintaining a ratio and other ways are present including consideration of viscosities, etc. The present invention is primarily concerned with the solute supply and its control as though the solvent supply provides a set factor. It contemplates monitor 32 and control arrangement 31 to assist in manually maintaining a constant ratio under widely varying municipal water and solute supply pressure changes. Preferably, the monitor 32 is conveniently supported in full sight at the outlet end 36 of the device 10 between the jet pump 24 and nozzle 12 and is connected between the solute supply tank 30 and solute supply valve 22 ahead of the jet pump 24. Its controls are adaptable for either right or left hand operation.

SOLUTE SUPPLY AND FLOW CONTROL

For the purpose of providing substantial constancy of the solute withdrawal pressure reflected in the mixture ratio of the first stage 24A of the pump, the storage tank may be a conventional bottle or container 30 and may be supported close to the level of the housing for portability and to minimize the lift height of the dip tube 39 of the solute. For this purpose a short flexible hanger strap as shown in Hechler, Ser. No. 443,831, is secured to the gun housing to carry the solute bottle and a short translucent tube 38 is provided between the dip tube 39 and a corrector means ultimately leading to the jet pump.

As shown in FIG. 1, the dispenser may be manipulated by one hand, either right or left, with the fingers around the housing 11 as a handle so that a person's thumb 41 is disposed in place to operate the manual flow control valve 14A having a stem 14B. Thereby, with the garden hose 20 and supply tube 38 being flexible, a person can manipulate, aim and direct the spray 13 in any direction or at any orientation without need for lifting or lowering the container 30.

Although the solute supply tube 38 could lead directly to the space 62 from the dip tube 39 and be manually attached and detached for the intermittent dispensing of water alone, contact of some insecticides and other solutes with a person's skin can cause injury or be dangerous to life itself. It is preferred to valve the solute simultaneously with the water through the selective connection 17, as already mentioned, and for this purpose the solute valve unti 22 is located on top of the housing just rear of the main valve actuator thumb handle 52.

Figure 2:
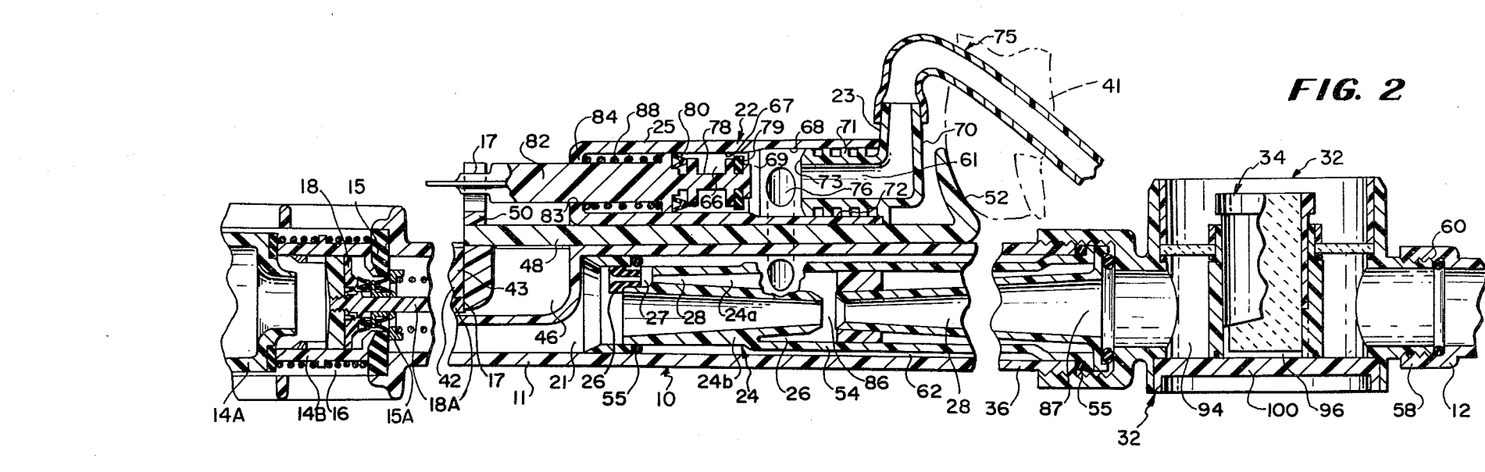
FIG. 2 is an enlarged longitudinal fragmented sectional view through the gun handle portion of the equipment shown in FIG. 1 with the elements in respective positions for full flow of both solvent and solute.

A valve chamber 66 in the valve housing 25 has two cylindrical portions 67 and 68 or different diameters separated by a tapering shoulder 69. The larger portion 68 opens towards the front of the gun where it receives an L-shaped conduit fitting 70 (FIG. 2) or T-shaped fitting 70T (FIG. 2A) whose inner end 71, or leg, is of the full housing diameter and is rotatively sealed in the mouth 72 of the valve chamber under negative gauge pressure during operation. The inner end 71 of the members 70 serves as a cut-off valve port land 73. The end of the arm 23 serves as a nipple that can be adjustably positioned over 180° on either side for the convenient attachment of a semitransparent solute supply hose 75 where the prime of the solute can be visually checked at a glance.

Figure 2A:
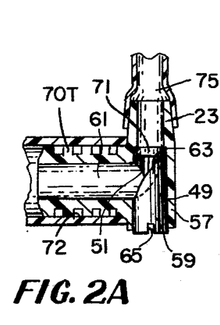
FIG. 2A is a sectional view of a modification of the base fitting shown in FIG. 2.

The modification 70T of the fitting 70 is essentially a T-fitting with the head end of the passage 61 in the leg portion providing a valve port 51 where it intersects the arm openings. A rotary valve 59 is mounted in the second arm with a slight frictional taper sealed journal 49 with an externally exposed screwdriver kerf 65, which also serves as an indicator, and a hollow inner end defining an L-passage 63 therethrough. A ring element 71 at the inner end journals the inner end so that the lateral opening coacts with the cylindrical concavity of the valve port 51. With this arrangement the T-fitting can be displaced 180° for left or right hand operation, and the rotary valve 59 is subjected to negative gauge pressure at the port for holding the valve in position. If the T-fitting is used in place of the L-fitting with a double stage pump, the valve 63 preferably is left wide open. Once adjusted either open for a two stage pump or partially closed for a single stage pump its repeated adjustment is rarely needed but can be by one hand holding a screwdriver and the other hand the device 10 where the comparison windows can be viewed.

The solute outlet opening 76 are disposed between the valve land 73 and the shoulder 69. A spool-like valve member 78 carries at one end a poppet valve head 79 coacting with the valve port 73 as a cut-off valve. Spaced from the poppet valve 79 and slidably engaging the smaller portion 67 of the valve chamber at all times in sealed relation is a piston 80 which confines communication between the L-fitting 70 and openings 76 to the larger chamber 68. The effective area of the piston 80 is substantially greater than the port area of the valve 73.

A valve stem 82 extends rearwardly out through a opening 83 in the rear end wall 84 of the valve housing 25 and selectively coacts with the T-head arm 50 be be optionally latched thereto by rotary movement of the solute valve 79 for either dispensing a mixture, if latched, or if unlatched, to be free from movement by the T-head arm 50 of the push rod 48 for dispensing solvent alone at the time the main valve 14A is opened by the push rod 48.

A mild effort coiled spring 88 interengaging the rear wall 84 of the housing and the valve wall 78 urges the valve to hold its closed position. This spring cooperates with any vacuum condition that may develop of the solute supply which may occur because of the aspirating effect of the jetflow of water when the main valve 14A is actuated by the push rod. In this connection, the area of the valve wall exposed to atmosphere is greater than that of the solute valve port 73 so that any drop in pressure in the large cylinder 68 will predominately hold the valve 79 closed. Therewith, during operation, the valve chamber with solute flowing is under moderate subatmospheric pressure and the load on the push rod can be quite modest. If solvent alone is being dispensed there is no solute vacuum load involved with the push rod even though the negative gauge pressure of the unsatisfied aspirating effect is quite deep.

PROPORTIONING AND MIXING

As noted, the valve compartment 68 empties into the space 62 where the jet pump unit 24 has one or more pumps. Two are illustrated by sections 24A and 24B which are arranged within a unitizing shell 54 for ready interchangeability for handling different chemicals or provide different proportions or flow rates. The exterior of the shell is spaced from the cylindrical wall of the space 62 in the housing as sealed at opposite ends with respect thereto by seals 55, as already described, to provide a wide inlet range for solute to accommodate all jet pump sizes. Otherwise, when not operating, this space is open to atmosphere through the first stage gap 27 and the diverging walls of both pumps.

A common inlet to the jet pumps for the solvent such as water from a municipal supply hose 20 is indicated at 21 and the solute is supplied to the solute space 62 through openings 76 from the nipple 70 which can carry a flow adjusting valve as described.

Each pump generally includes an entrance for the water under pressure followed by conveying walls of the jet nozzle 26 that converts pressure into jet flow energy and terminates in a throat at the gap 27. The flow of solute to the gap 27 is induced by aspiration at the gap and provides a negative gauge pressure on the solute supply in relation to lift height or controlled flow restriction. This relationship can be multiplied in parallel or in series arrangements. Thus, the negative gauge pressure can approach a deep vacuum condition as low as 1 or 2 p.s.i.a. depending upon the lift height of solute from a supply tanic 30, or its rate of flow, or both, and can substantially vary the ratio proportion of the resulting solution mathematically in any one of several ways. Leading from the gap is a larger passage for mixing having diverging walls 24A which converts turbulence back to pressure. The ultimate ratio is then completed in the second stage pump in which the diverging walls can be shortened if a soft flow discharge is desired for the mixture.

Thus, the solute is aspirated, diluted and mixed with solvent at a given primary ratio approximately 1 to 3 for optimum accuracy and said mixture at a substantially constant pressure is then further diluted for the final ratio, mixed for discharge at the outlet 87 of the housing in the required ratio, and dispensed ultimately through the nozzle 12. Any substantial degradation of efficiency i.e. pressure drop, which structural design may be required is divided essentially equally between the two stages in a design involving length and size of a downstream pressure having conical shape portion with an included angle of approximately 6°. The first stage pilots the second stage for best overall results since pressure and flow rate therebetween are substantially constant.

The joint action of the jet pumps, accordingly, are capable of dispensing a quite accurately proportioned solution at optimum efficiency through a fixed nozzle at the output end at constant pressures and rates of flow well above 5 p.s.i.g. Below this pressure the springs and the valves in the valve chamber 18 act, as already described, and the solvent chamber is safety vented to prevent contamination backflow.

PROPORTION RATIO MONITOR

Proportions do change, or changes are desired from time to time, with different pressures and different solutes and means are provided in the present invention for monitoring.

If a homogeneous radiation transmitting absorbing medium disposed between parallel planes normal to a parallel beam of energy is considered to be a plurality of contiguous layers of uniform thickness, each layer absorbs the same fraction of the radiation energy incident on it. (Lambert's Law). Each individual molecule of the absorbing material absorbs the same fraction of the radiation upon it no matter whether the molecules are closely packed in a concentrated solution or highly dispersed in a dilute solution, (Lamber-Beers Law). This is subject of course to variables in temperature, wave length of radiation and the solvent and subject to only parallel rays being used which requires scientifically sophisticated lighting, lenses and fast dyes.

In the present invention these variables are minimized virtually to zero by a contiguous proportioning, mixing and monitoring of the ratio being accomplished in a fraction of a second, almost simultaneously, at a speed engendered by the safety anti-backflow positive working pressure provided for the invention fpr adequately high rates of solvent flow during operaton. Moreover, fadable dyes can be used as well as fast dyes.

Ample lumens of scattered rays without parallel beam lensing equipment are available from ordinary light sources to illuminate target windows of the invention from which scattered rays are emitted directly into and through two homogeneous bodies of radiation absorbing media of different thicknesses or transmissivities disposed between parallel planes. Also as distinguished from being parallel (Lamber-Beers), the rays passing from the illuminated targets to the pupil of the operator's eye converge in the absorption media in frustum patterns F of different heights and pass through reduced openings located approximately three inches from the targets with eye E (FIG. 24) located approximately 20 inches from the targets. Although the increasingly narrower area of the successive "layers" in each frustum, which are due to the angles of light convergence, may in effect comparatively diminish the resultant "fraction" of absorption factor that is found with theoretically parallel rays, this diminishment factor is substantially counteracted by the acuteness of convergence angles marginally increasing the distance of travel of the converging rays through the absorbing media.

No lenses are required, only a sample prism P may be used in one line of sight to converge it to the other at said twenty inches merely to avoid the need of moving the eye back and forth in comparing the targets. Thereby, the relative ratio of solvent and absorbing material in the resulting solution can be checked quickly and accurately with the absorbing material itself at a controlled transmissivity thickness. The convergence angle is small enough that possible marginal darkening of any image is not visually significant. If much wider-target areas were required, the parallel windows can be convexly curved on a radius equal to the viewing distance if desired.

Figure 15:
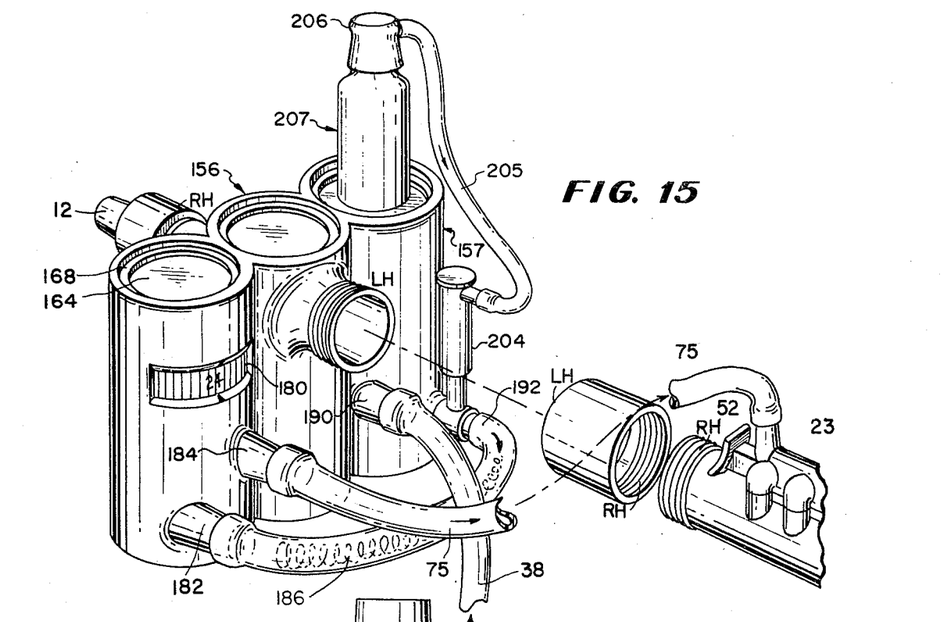
FIG. 15 is a partially exploded perspective view of a unitized monitor and tracer supply showing the hose connections and method of attachment to a proportioning gun.
Figures 16, 17:
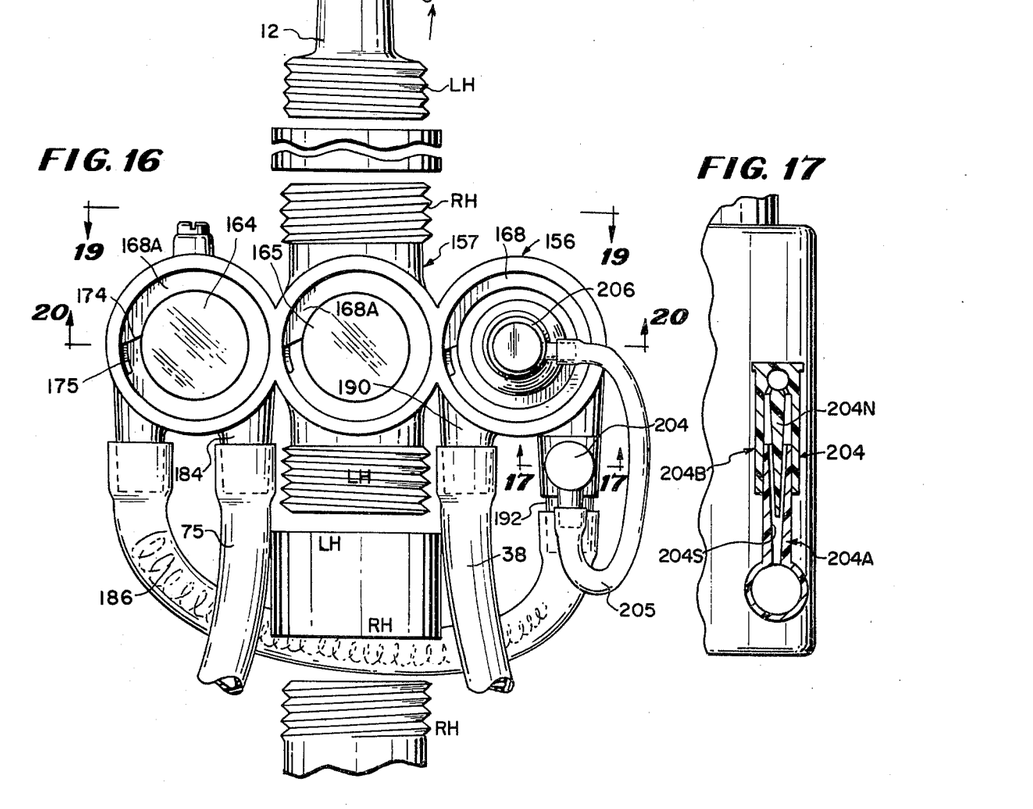
FIG. 16 is a partially exploded plan view of the monitor shown in FIG. 15.
FIG. 17 is a sectional view taken upon line 17—17 in FIG. 16 showing the preferred tracer supply valve construction.
Figure 18:
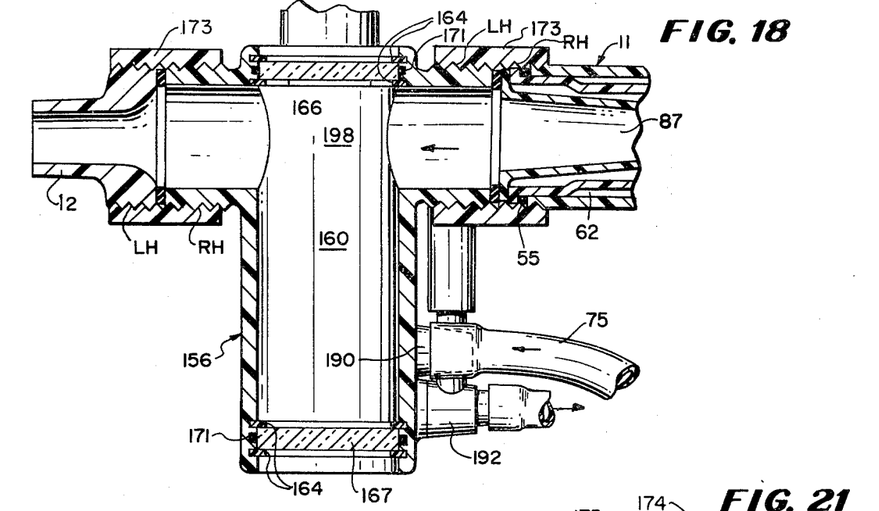
FIG. 18 is a vertical sectional view taken centrally through the monitor with the exploded parts of FIG. 15 secured ready for operation.
Figures 19, 21:
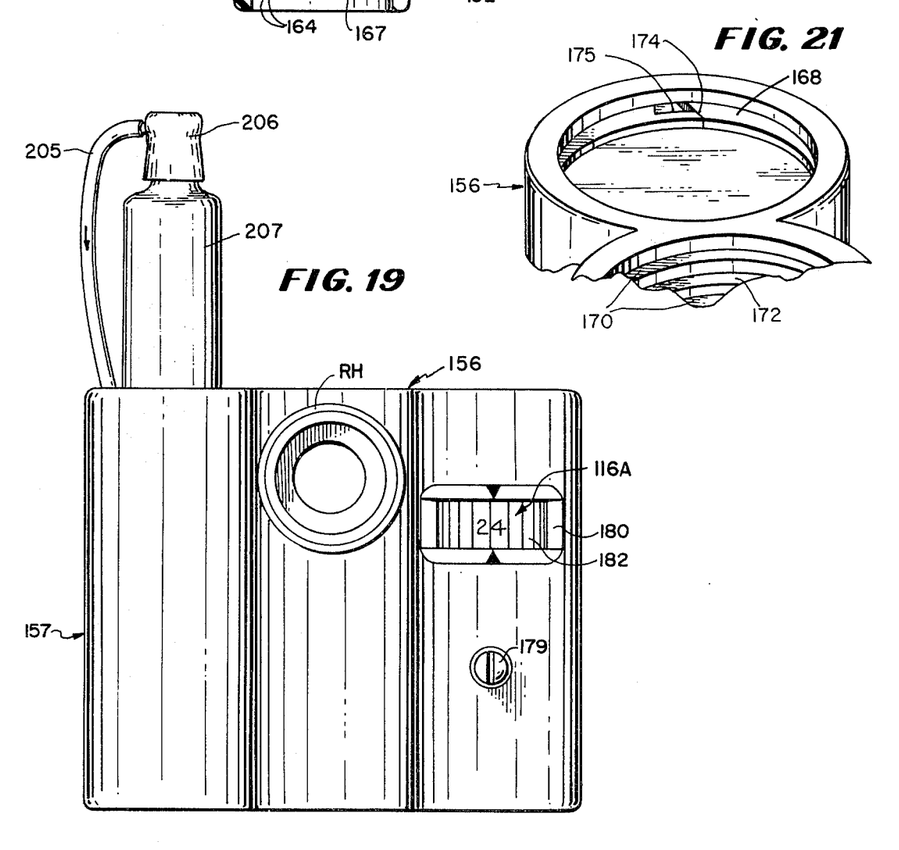
FIG. 19 is a side elevational view taken from the front of the monitor shown in FIG. 15 as indicated by line 19—19 in FIG. 16.
FIG. 21 is an enlarged perspective view of the snap ring means for holding the windows in place.

For these purposes, a monitor 32 is provided between the nozzle 12 and the outlet end 36 of the housing along with a solute flow control 31 with a single stage pump for applications where an accurate ratio proportioning must be assured at the gap 27 of a jet pump regardless of changes in pressures of solvent or solute, or both, Moreover, the monitor in one of its embodiments 56 (FIG. 11) serves to operate with pre-dyed solutes and an auxillary dye supply, if necessary, whereas in the other embodiment 156 (FIG. 15) a concentrated F.D.A. approved dye tracer reservoir is a part of the monitor in which the tracer is injected with solutes intermittently or continuously when bulk solutes are not adequately pre-dyed.

Figures 3, 4, 5, 6, 7, 8, 9:
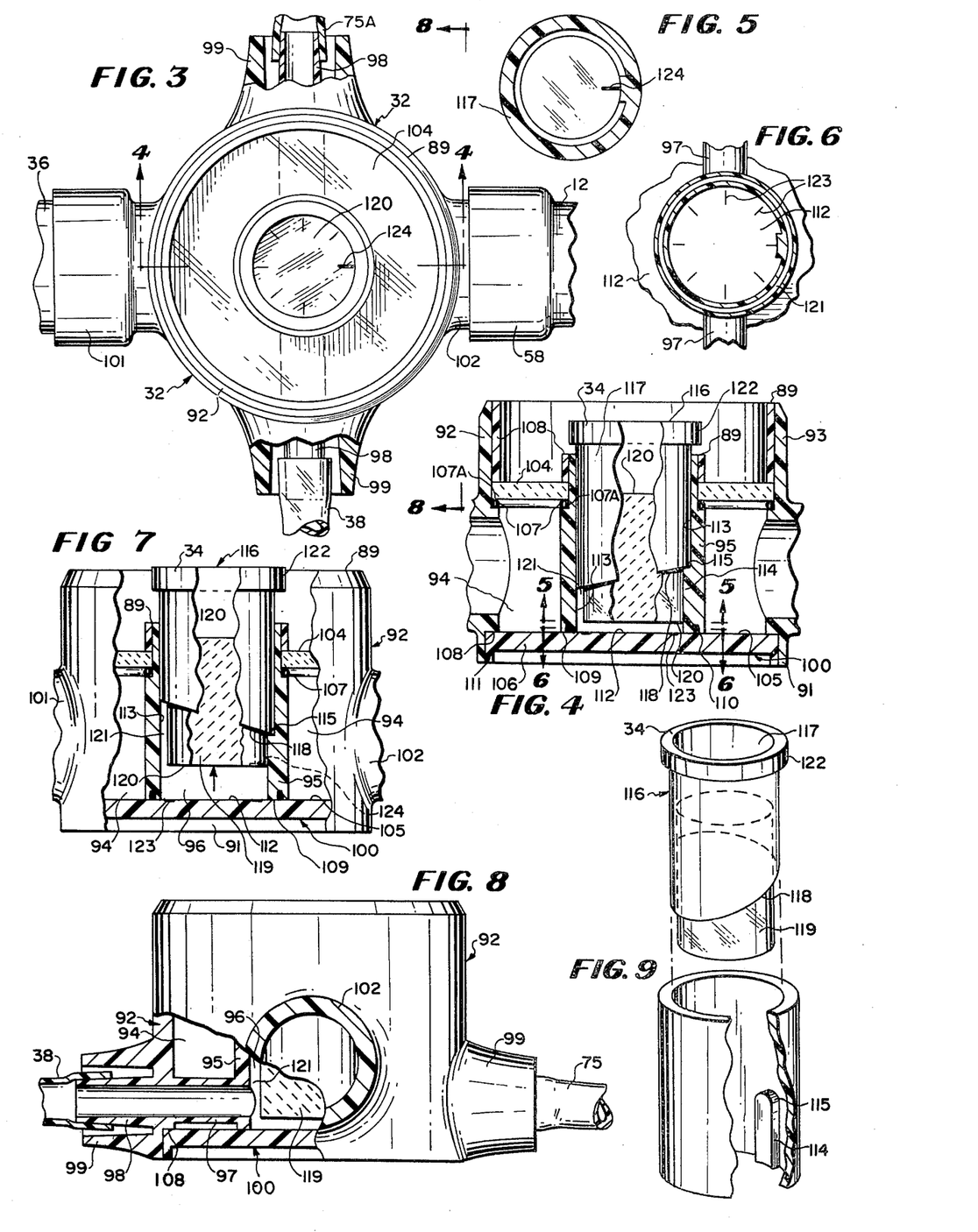
FIG. 3 is a top view of the monitor portion of the embodiment.
FIG. 4 is a sectional view taken on line 4—4 in FIG. 3.
FIG. 5 is a sectional view taken on line 5—5 in FIG. 4.
FIG. 6 is a sectional view taken on line 6—6 in FIG. 4.
FIG. 7 is a side elevational view partly in section showing the adjustability of the monitor.
FIG. 8 is a section taken on line 8—8 in FIG. 4.
FIG. 9 is an exploded view of a depth adjusting arrangement illustrated in FIG. 7.

In the monitor embodiments 32 and 56, a housing 92 is provided having concentric chambers 94 and 96 (FIG. 7), one of which is supplied with solute and the other with the solution being dispensed. Preferably, the housing is molded to be open at both ends with a conduit 97 (FIG. 8) extending from the outside through the outer wall 93 and through the cylindrical chamber 94 and inner wall 95 to conduct solute through the inner chamber 96. The conduit 97 terminates externally with nipples 98 to receive hoses 75 and 38 or 146 in sealed relation. The nipple connections are protected by sleeves 99. The outer wall of the housing is externally shaped on one side with a female coupling 101 to be secured to the discharge end 36 of the housing and on the other side of the housing receives the nozzle 12 as secured to a male threaded coupling 102 so that the solution passes laterally through the outer chamber around the inner chamber before being discharged through the nozzle 12.

Precisely spaced ring windows 104 and 106 are provided at opposite ends of the housing and rest on internal flanges or shoulders on the walls forming the chambers 94 and 96. The upper ring window 104 (FIG. 4) is preferably transparent and rests on shoulder 107 as sealed by O-ring 107A and held in place by retainer sleeves 108 terminally heat fused at 89 with the walls 93 and 95 in a unitized construction.

The ring window target area 105 is a portion of a single translucent member 100 that closed the lower ends of both chambers as supported on the shoulders 108 on the outer wall 93 and resting against the lower end 109 of the inner wall 95 as sealed by O-ring 110. The margins of the member 100 and the outer wall 93 are heat fused as at 111 in unitized relation after assembly to provide a flange 91 that protects the member 100 from being scratched. The central portion of the member 100 serves a target window 112 for the inner chamber 96. The translucency is for admitting uniformly diffused light as a background screen serving as a target, and the transparency for clear viewing.

The inner face of the inner wall 95 is cylindrical to provide a sealing, sliding and rotational surface 113 which as formed also has an offset 114 defining a micrometrically correctable cam follower 115 thereon for spacing it a predetermined distance from the window 112. A viewing cup 116 is received in the inner chamber 96 and comprises a sleeve 117 rotatably and slidably engaging the surface 113 with its lower edge defining a spiral cam 118 of approximately 300° engaging the cam follower 115 for axial displacement thereby upon relative rotation.

An upper transparent window 120 for the inner chamber is carried at the lower end of the sleeve 117 and comprises a transparent section of a glass rod 119, polished on opposite ends, that is secured to and extends below the sleeve 117 to provide a solute flow space 121 around it as well as between the windows 112 and 120. The upper end of the sleeve 117 has a flange 122 on it to serve as the manual actuator of the cam for the comparator control 34. Relative rotation between the cam 118 and follower 115 varies the depth of the central chamber by raising or lowering the viewing cup 116 and this can be measured in lineal increments but preferably in increments indicating relative depth proportions between the inner and outer chambers 96 and 94, respectively.

For this purpose radial graduation markers 123 (FIG. 6) may be provided on the inner face of the lower window 112, and a single market 124 on the upper window 120 to determine the mixture proportion desired, or, to check to see what proportion is being provided if the monitor windows do not match either purposefully or as a happenstance. It is appreciated that spacers (not shown) of either a regular thickness or odd thickness for set proportions can be dropped in place between the windows 112 and 120 with or without the cam operation being used.

The sealing relation between the viewing cup 116 and inner wall surface 113 is by a grease type film essentially inert to chemicals expected to be handled. In the arrangement other viewing cup restraint is not required. Accordingly, the viewing cup can be easily removed and returned to operative position. Any solution under pressure is confined to the outer chamber 94 having fixed walls while the inner chamber 96 is subjected to a negative gauge pressure due to aspiration which holds the viewing cup in place and cam elements in contacting relation. Moreover, it is readily possible to match the spiral cam suitably if any cam slippage might be incurred during operation.

As already noted, the ON-OFF control of the volume of solute delivered in a given time, whether referred to by "rate" or "quantity" may be associated with the fitting 70 as a part thereof but one embodiment comprises an adjustable needle type valve 31 telescoping in a sleeve for use with a single stage pump. One of the connecting conduits is a resilient hose 75A that engages both valve elements so that they can be axially adjustable resiliently with respect to each other in the hose 75A while the other hose portion 75B is secured to only one of the elements to complete the hose connection 75. Adjustment of the valve is not frequent and in the position shown it is the least likely to be accidently disturbed. Thus, adjustment of flow to provide a proper mixture proportion does not materially change the negative gauge pressure in the inner chamber 96 that is generally subject to the lift height of the solute notwithstanding a possible occasion when the solute supply might be above the level of the comparator.

Thereafter, once it is determined what the ratio of the proportion is to be and the solvent has been treated with a tracer, the depth of the solute chamber 96 can be set exactly in relation to the fixed depth of the outer chamber 94 in that ratio desired for the solution. Then when the solvent supply is turned on at the main valve 14A the adjustment of the metering valve 31 can be made and corrected from time to time so that the tracer effects observed in the chambers 94 and 96 match. Thereby, a correct ratio proportion of the solute and solvent can be assured at all times to prevent any degradation of the mixture due to changes in pressures and relative heights. Furthermore, for versatility, the proportion ratio can be held very close for any one of a number of ratios and such ratios can not only be standardized in the chemical industry to supply less diluted solutes but the selections can be made regardless of the trademark or government required coloring of the solutes.

In the case of a set ratio, the metering valve 31 in its ultimate function adjusts the ration and counteracts any critical changes in pressures on solvent or solute by controlling the flow rate of the solute, or, varying the pressure drop across it with respect to the solute aspiration pressure. Briefly, a null point adjustment related to the relative chamber depths determines the ratio, the metering valve corrects for pressure situations and viscosity, and in combination with the nozzle output controls the rate of flow.

An example would be to maintain the same proportioning ratio when changing the size of the jet pump or pumps. The meter valve can be quickly adjusted empirically to assure the ratio desired merely by comparison of the appearances at the two windows.

It is to be noted in this connection that the color density in a space .010 deep would be and appear to be the same as its color density in a solution one inch deep that has a 1 to 99 parts ratio, or 1% proportion, a thorough progressive mixture as provided herein having been assured before the optical comparison. Furthermore, if a ratio is required to be accurate within plus 5% and negative 0%, the depth adjustment in the solute chamber can be increased appropriately 2.5% and the null point matching can be kept within the desired range as where it is important that a dilution should not exceed a certain ratio. On the other hand, if solute must be kept below a certain ratio, the depth adjustment in the solute chamber could be increased enough to stay within the safe limit.

It is also to be noted that since the adjustment of the solute depth is micrometric, it may be well to have the solute chamber depth at a determined constant and adjust the depth of the solution chamber. This would be macrometric with a greater degree of ultimate accuracy.

TRACER SUPPLY

It has been noted herein that the amount of tracer in a solute is not essentially critical and can be supplied either originally with the solute; or, it can be later added to supplement characteristic trademark coloring supplied with the solute; or, it can be completely supplied as an additive at the time of dispensing where the solute provided has no pre-added tracer. It is preferred to add a tracer at the time of dispensing so that a specific or special form of energy transmission for selected sensors can be used, if desired, to provide the optimum level of energy detection for determining the exact proportion or matching in the comparator chambers as already described.

Figure 10:
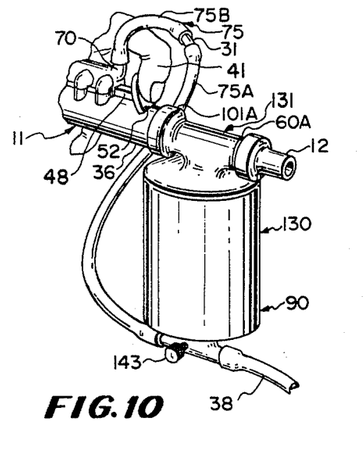
FIG. 10 is a view similar to FIG. 1 illustrating a portable supply of concentrated tracer mounted by itself in position on the gun if colored solution is all that is desired.
Figure 11:
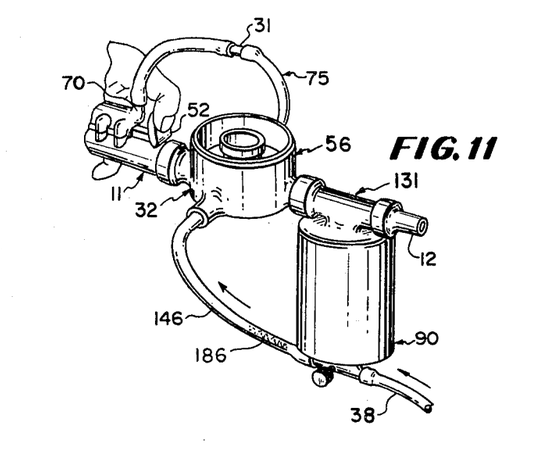
FIG. 11 is a view similar to FIG. 10 illustrating the cooperating relation of the portable tracer supply and the monitor if tracer is added to optimize comparison.
Figure 12:
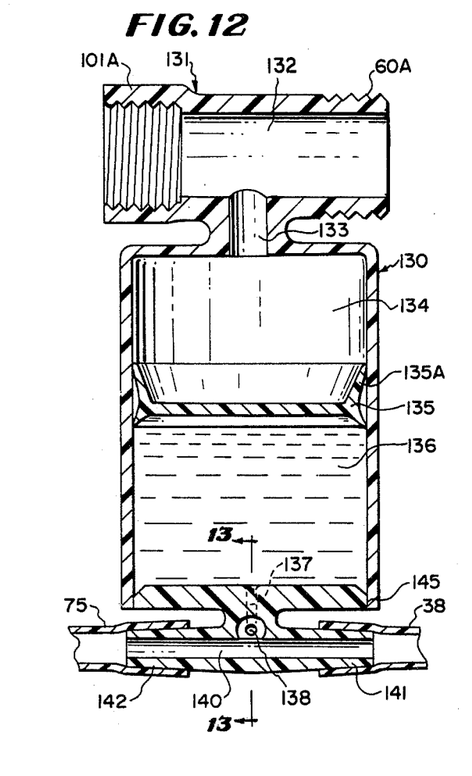
FIG. 12 is an enlarged central sectional view of the structure of the portable tracer supply.
Figure 13:
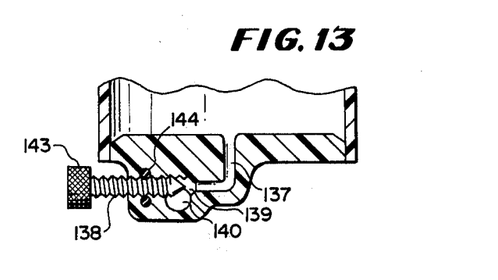
FIG. 13 is a section taken upon line 13—13 in FIG. 12.
Figure 14:
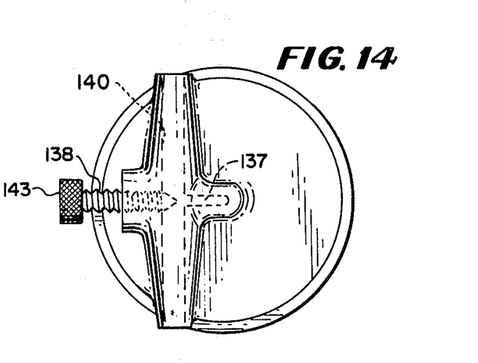
FIG. 14 is a section taken longitudinally of the adjustable valve for the tracer supply.

Referring to FIGS. 10, 11 and 12 a device for adding a highly concentrated tracer in small amounts to the solute is illustrated in FIG. 12 for use separate from a comparator (FIG. 10) or, along with the comparator 32 (FIG. 11).

The tracer supply device includes a unitary container 130 which can be used as a throw-away member and has a T-shaped coupling section 131 which is secured directly to the outlet end 36 of the gun housing 11 by a female coupling 101A, and, it has a male thread 60A at its outlet end for connection to the monitor 32 or nozzle 12. The nozzle 12 provides a back pressure on the solution being discharged through it to provide a positive pressure on the lateral passage 133 which leads to a cylindrically walled tracer chamber 134 ahead of a pressure sealing flange 135A on a freely moving piston 135 that bears downwardly on the supply of tracer 136 stored below it.

At the bottom of the chamber an outlet passage 137 leads to a needle valve 138 whose outlet 139 connects to a through passage 140 that terminates at opposite ends in identical nipples 141 and 142 to receive the hose 38 on either nipple and the hose 75 on the other nipple (FIG. 10) or conduit 146 (FIG. 11). The needle valve 138 is manually operated by an indicator member 143 and sealed by an O-ring 144. The valve stem and seal 144 can either be exposed to conduit 137 upstream of the confluence or it can be located as shown downstream thereof depending on whether the O-ring 144 is to be exposed primarily to the tracer or solute, respectively. It is to be noted that the device illustrated can be molded as a two unit housing which will receive the piston 135 and be heat sealed at the joint 145 to form the chamber 134. The valve 138 with the O-ring is then installed and the tracer chamber 136 below the piston 135 first exhausted of air by pressure applied above the piston 135 and then filled with liquid tracer through the passage 140 by then applying a vacuum above the piston 135. Thereafter, the valve 138 is closed to seal a charged package of concentrated tracer 136.

In operation a pressure differential across the piston 135 will not exist until the solution is being dispensed. The back pressure will be developed by the nozzle 12, and, a negative pressure will exist in the solute passage 140. Thereafter, if necessary, valve 138 adjustment will provide the tracer intensity that optimizes the comparison of the amount of solute that is being introduced into the solution.

In FIG. 10 the embodiment is illustrated in which the monitor 32 and the dye supply device are connectable in tandem between the jet pump 24 and the nozzle 12. In FIG. 11 the relative positions which includes the monitor 32 are substantially immaterial as long as the solute supply hose 38 is connected to one of the nipples 141 and 142 of the tracer supply and the other nipple is connected by hose 146 to one of the nipples 98 on the monitor with the other nipple connected to the conduit 75 which in turn is connected to the fitting 70 as already described.

With solute flowing through the hoses 38, 146 and 75 and solvent flowing through the jet pumps 24, both solute and solutions will be flowing through the monitor 32. Solution flowing under pressure through passage 140 will then develop, as already explained, a pressure effective upon the piston 135 ahead of the conduit 132. This effect will be almost immediate with the opening of the main valve 18 in the gun if adequate working pressure is present on the solvent supply.

Thereupon, the needle valve 138 can be opened to bleed tracer into the solute and such will be mixed to provide a coloring for the inner chamber 96 and the outer chamber 94 of the monitor 32. If the tracer effect is not bright or dark enough for optimum comparison conditions, the valve 138 is adjusted until such conditions are presented. Then if a mismatch clearly appears, the restriction means 31 or rotary valve 59 can be adjusted to provide the desired mixture proportion as already described or the viewing cup (34 or 116A) can be adjusted until the existing ratio is indicated. A conically wound wire is provided in the conduit 146 to assure homogeneity of solute being viewed in the comparison compartment.

UNITIZED COMPARATOR AND TRACER SUPPLY

Referring to FIGS. 15–24 the arrangement illustrated in FIG. 11 is a unitization of the monitor and tracer supply. It also includes means for making momentary checks on the proportioning as well as with continual use of the tracer in a dispensing operation.

The monitor-tracer modification unit 156 has a molded housing 157 defning three contiguous circular compartments 158, 160 and 162 (FIG. 20) open at both ends, with two adjacent ones, 158 and 160, closed at the top by circular transparent viewing windows 164 and 166 and the lower ends of all the three compartments closed by translucent circular windows 165, 167 and 169 either fritted or coated to provide scattered light viewing targets. All windows and closures are supported between snaps rings 168 (FIG. 20) received in spaced grooves 170 and are edge sealed by O-rings 171 received in intermediate grooves 172. The rings 168 are split on an angle 174 and the outer corner notched as at 175 to receive a screwdriver bit for removal.

Figure 20:
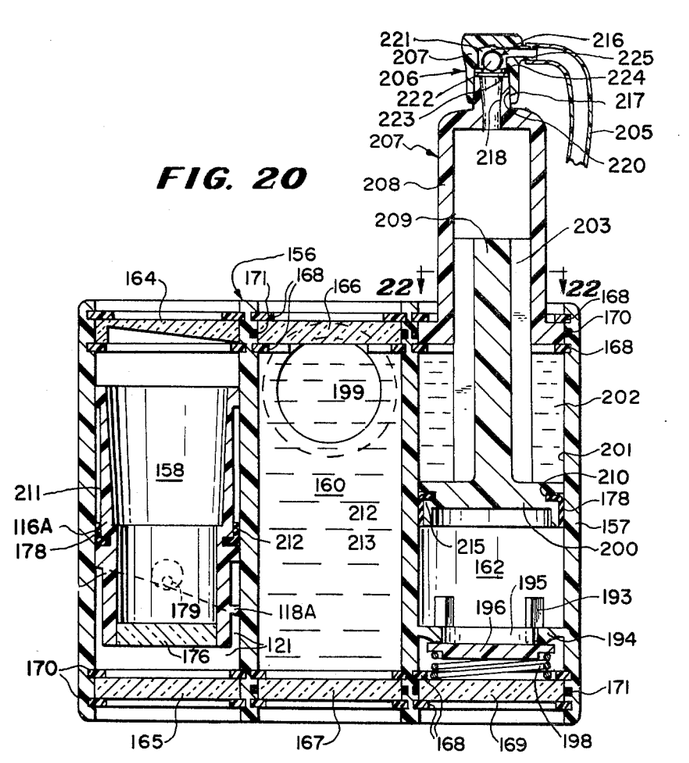
FIG. 20 is a sectional view taken in line 20—20 in FIG. 16.

The compartment 158 rotatively receives a hollow viewing cup 116A (FIG. 23) that has a transparent window 176 at its lower end. A spiral cam rib 118A (FIG. 23) formed on the side of the cup 116A coacts with an eccentrically adjustable follower 179 rotatably mounted on the wall of the compartment 156 for manual actuation to vary the effective space between the windows 165 and 176 (FIG. 20). A low friction deformed seal 178, seals the cup 116A at the compartment wall for its adjustable movement. This movement is accomplished manually by finger contact through side openings 180 (FIG. 19) in the compartment wall where also is displayed a mixture ratio scale 182 on the wall of the cup 116A. Negative gauge pressure generally maintains cam engagement in its adjusted position. As viewed in FIG. 15 an elevated outlet nipple 184 located through the wall of chamber 158 is connected by hose assembly 75 to the fitting 70 or 70A (FIG. 1) to assure removal of all bubbles from the space 121 between the windows 165 and 176.

Figures 22, 23, 24:
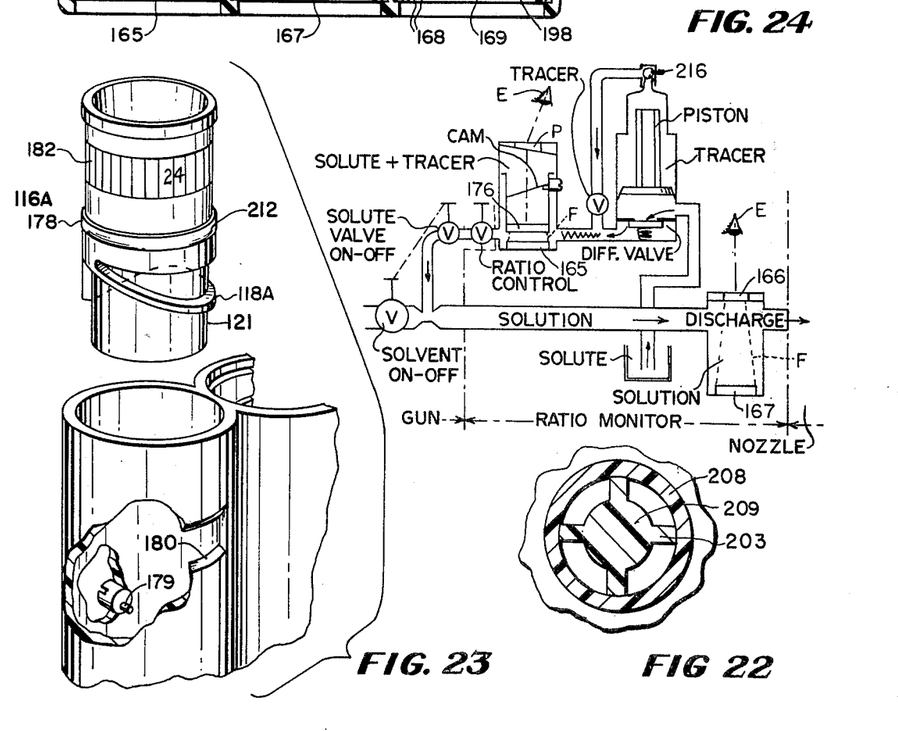
FIG. 22 is a section taken upon line 22—22 in FIG. 20.
FIG. 23 is an exploded view of the elements involved in the cam adjusting piston.
FIG. 24 is a diagrammatic illustration of the respective elements and their operation in the unitized embodiment.

Referring to the low friction seal 178 and FIGS. 20 and 23 sectionally illustrating it, a flat ring seal member is cut from a sheet of moderately soft elastomer having a thickness approximately 1/32 inch. The radial groove 210 provided in the cup 116A is of substantial depth and one wall adjacent thereto is relieved as at 211 to a radial depth from 1/32 inch to 3/64 inch with an axial length of 3/32 inch for a cup 116A approximately 1 inch in diameter leaving a square corner 215. The hole in the washer is substantially less than the inside diameter of the groove 210 and therefor is stretched substantially when installed. The free edge 212 then folds down towards the relief 211 to a steep conical shape with the edges forming a cylindrical flange 213 without any wave form in the edge. The seal 178 must be thin and the corner 215 quite severe leaving a space for the seal to occupy that is only a few thousandths of an inch which measurement is approximately the clearance of the cup itself from the cylindrical wall.

The middle compartment 160 provides a full flow passage 199 from the gun housing 11 and outlet 87 through the chamber 160 to the nozzle 12, it being noted (FIG. 18) that the threads on outlets 87 and 186 of the gun 11 and comparator 156 are right hand threads as indicated by RH and the inlet threads 187 of the comparator 156 and nozzle 12 have left hand threads marked LH to avoid improper orientation of the three parts. As advantage is derived by the RH threads being a little longer than the LH threads so that make-up by matingly threaded couplings 173 can be started one turn on the RH threads and then receive the LH thread engagement for the rotation and tightening of the couplings 173 while the parts are being assembled as held in proper orientation while the coupling is tightened. If desired, the nozzle 12 thread can be RH without need for coupling, depending on the economics of manufacture.

The third compartment 162 serves as a tracer supply reservoir 201 having vertically spaced inlet and outlet nipples 190 and 192, respectively, located near the bottom window 169. A partition 194 inside the compartment 162 between these openings defines the tracer reservoir 201 above it and has a backflow check valve 196 closed by a spring 198 which opens with pressure-flow of solute from above it through inlet nipple 190 to outlet nipple 192 to develop a flow pressure drop across the check valve that is constant.

A piston 200 mounted in the tracer reservoir 201 is subjected to the higher pressure on its lower side and carries a tracer supply 202 on its upper side that is subjected to said lower pressure through an adjustable metering and shut off valve 204 (FIGS. 15-17) in a conduit 205 that interconnects the upper part of the reservoir 201 to the outlet nipple 192. Another low friction seal 178 is provided on the piston 200 which requires only a few ounces pressure differential to move the piston. The pressure differential thereby provided serves to induce the introduction of tracer 202 into the solute as metered by the valve 204. This valve has telescoping members. The cylindrical frictional fit between two elements hold the set of the valve and one of the elements 204A (FIG. 17) carries a tapered valve seal 204S, the other 204B carries the needle member 204N.

Relative movement of the parts of the valve 204 is accommodated by the flexible hose 205 which interconnects fitting 206 carried by a transparent closure member 207 which in turn is marginally received by snap rings 168 and an O-ring seal 171 to seal the tracer reservoir 201. The close member 207 includes in guided relation a hollow cup 208 telescopically receiving the upper end of the rod 209 carried by the piston 200 which serves as a visible indicator of the amount of tracer 202 remaining in the reservoir 201.

Referring to FIG. 20 the upper end of the closure member 207 is externally tapered at 217 so that it can be wiped clean, when desired, and is also internally tapered at 218 to receive the nozzle of a tracer replenishing supply container when required (not shown). The wall of the nipple fitting 206 is internally tapered at 220 to mate with the taper 217 in sealed supporting relationship. Above the tapered securement the wall terminates internally in a valve chamber 221 enclosing a ball 222 that is held in place by a valve seal ring 223 that is pressed into place against a shoulder 224. The outlet from the chamber 221 is through a nipple 225 receiving the hose 205. Whenever the supply of tracer is to be supplied, the closure 201 is removed to receive the tracer replenishing nozzle and then returned to place without need for touching any tracer covered surfaces.

In operation, reference is made to FIG. 24 where water under municipal pressure as a solvent is supplied through the gun housing 11 under at least 5 p.s.i. as controlled by the main valve 18 through venturii gaps 27 and 86 of the jet pump, and from there through the compartment 160. Solute is supplied under atmospheric pressure through the tracer chamber 201 beneath the piston 200, through the pressure differential valve 196, past the outlet of the tracer valve 204 and through the cammed variable space 195 between the windows 165 and 176 in compartment 158, then into conduit 75, through the ratio valve 31 and the manual valve 73 to the venturii gap 27 where it is mixed with the solvent. Varying the valve 31 varies the negative gauge pressure at the gap 27 and thereby varies the mixture passing through compartment 160 between windows 166 and 167.

If the solute has adequate pre-added tracer in it for making the comparison of light transmissivities view through windows 165 and 166 the tracer valve 204 can remain closed because matching the light transmissivity of the liquids in compartments 158 and 160 indicated the ratio being dispensed as read on the cammed scale 182 and as provided by the adjustment of valve 31. In fact, the paths of flow of solute and solution being the same as described with the respective connections of the tubes 38, 146 and 75, then, in event added tracer is not desired, at all, the monitor can either be removed or the solute tube 38 can be connected directly to the monitor solute inlet nipple 190, and the tube 75 to the outlet nipple 192 in which event the manual valve 31 is untouched and the needle valve 204 is closed tight. On the other hand, if the pre-add tracer is dim, or there is none pre-added, the tracer metering valve 204 can be opened and adjusted to provide any intensity of tracer coloring desired, and, matching of energy transmissivity can be accomplished with great accuracy.

The matching is accomplished either by adjustment of the valve 54 or the piston 116A by cam movement as mentioned and is viewed through the windows 164 and 166. The ratio of thicknesses of the liquids viewed indicates the mixture ratio of the dispensed liquid.

The window 164 preferably is a prism converging the viewing sight centers for the eye at about 18 inches for convenience of viewing without the operator moving his head back and forth for the comparison.

By utilizing the pressure of the solvent in aspirating the solute their ratio will remain substantially constant under given flow control openings and by utilizing a modest pressure differential developed with the solute flow a tracer may be supplied to the solute through a variable orifice at a feed rate to optimize the amount of tracer for purposes of the comparison relating to the ratio or proportion of solute to solvent which can be completed within seconds between the introduction of the tracer and the making of the comparison.

What is claimed is:

1. In combination with a device dispensing a solution under pressure, a housing defining a compartment having a chamber for a tracer dye,
    piston means mounted in sealed relationship in said chamber separating it into at least one collapsible compartment;
    means for supplying pressure against said piston means to collapse said compartment and including a flow passage supplied by at least one of said solution elements having a flow restriction downstream from said chamber, and
    means for delivering tracer dye from said collapsible compartment to a conduit conducting solute at a pressure less than said supply pressure and including a passage having a flow control valve at the outlet of said collapsible compartment and connected to said solute conducting conduit.

2. The combination defined in claim 1 including means controlling simultaneous flow in said passages including a valve controlling flow of solvent in the first passage and means introducing the tracer dye into said solute supplied to said solution.

3. A tracer supply means comprising a housing having a storage chamber for a tracer dye.
    piston means slidably mounted in sealed relationship in said chamber separating it into at least one contractible reservoir compartment,
    liquid means for applying pressure against said piston to contract said compartment and including a liquid flow outlet passage having a flow restricting means downstream of said reservoir compartment,
    valve means controlling outflow of tracer dye under presure from said reservoir compartment.
    conduit means for conducting flowing liquid in communication with the tracer dye outlet of said valve means, and
    means for controlling simultaneous "flow" and "no flow" conditions of said liquid means and tracer dye flows.

4. A tracer dispensing supply means comprising a body having a chamber for storing a tracer having openings at opposite ends,
    piston means mounted in sealed relationship in said chamber between said openings separating it into at least one collapsible compartment to discharge tracer therefrom through one of said openings in predetermined amounts including a valve controlling the flow,
    means for mixing the tracer with a stream of flowing solute,
    means for mixing the solute with a solvent under flowing pressure of the solvent to provide a flowing solution,
    conduit means conducting the flowing solution in communication with the other opening, and
    flow controlling means downstream of said other opening inducing a pressure upon said flowing solution effective through said other opening to urge collapse of said compartment to discharge tracer therefrom to said flowing solute.

5. The combination called for in claim 4 including valve means for controlling the discharge of tracer and controlling the flow of solvent to said solute.

* * * * *